United States Patent [19]

Stern

[11] 4,159,179

[45] Jun. 26, 1979

[54] COLORIMETER

[75] Inventor: David L. Stern, Baltimore, Md.

[73] Assignee: The Baltimore Spice Company, Baltimore, Md.

[21] Appl. No.: 802,601

[22] Filed: Jun. 2, 1977

[51] Int. Cl.² ............................................. G01J 3/50
[52] U.S. Cl. ................................... 356/411; 356/414
[58] Field of Search .................. 356/72, 73, 181, 201, 356/204–206, 244, 246, 409–411, 414; 250/573–576

[56] References Cited

U.S. PATENT DOCUMENTS

| | | | |
|---|---|---|---|
| 3,010,798 | 11/1961 | Whitehead et al. | 356/72 X |
| 3,503,683 | 3/1970 | Isreeli et al. | 356/181 |

Primary Examiner—F. L. Evans
Attorney, Agent, or Firm—Lawrence I. Field

[57] ABSTRACT

An improved Colorimeter which can be used to analyze samples in either a stationary mode (e.g. in a test tube) or in a flow-through mode wherein the sample flows through the apparatus. The Colorimeter is equipped with means to direct the illuminating radiation selectively to either mode of sample.

2 Claims, 1 Drawing Figure

U.S. Patent  Jun. 26, 1979  4,159,179
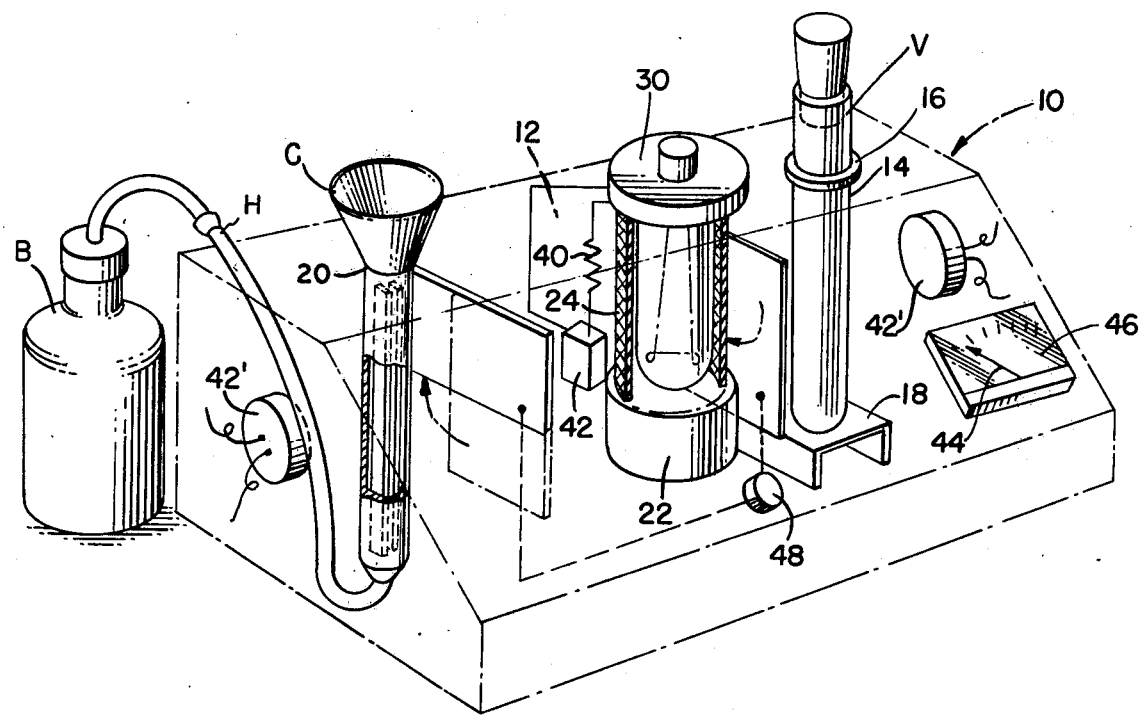

COLORIMETER

This invention relates to an improved colorimeter. More particularly it is directed to a colorimeter which can be utilized to measure samples in either (1) the stationary mode, i.e. wherein the measurement is made of a sample in a test tube or cuvette and (2) a flow through mode, wherein the sample flows along a path which intercepts the beam of radiant energy passed through the sample to a detecting means.

For many measurements it is convenient to utilize a sample in a stationary mode, i.e. in a test tube. The advantages of this mode of operation are that the apparatus is relatively simple, and is sufficiently accurate for many purposes. The disadvantages are that the optical properties of test tubes vary over a wide range and affect the results. Further the sample may be too concentrated and require dilution, or the sample may be a suspension difficult to maintain uniform.

As a consequence colorimeters have been devised in which the sample is measured as it flows through a specially designed curvette. Such devices are particularly useful when the quantity of sample is limited but they have a set of disadvantages peculiar to themselves. Piping must be utilized to collect the sample after it has run through the cuvette, means must be provided for flushing all of one sample from the cuvette before an accurate measurement can be made on a succeeding sample.

The present invention is addressed to an apparatus in which both kinds of colorimetric measurements can be made on a single scale, by merely throwing a switch so that the light path is through either of two kinds of sample tubes.

The invention will be better understood from the description which follows, taken with the drawings in which the single FIGURE is a schematic view of the apparatus, in perspective.

The apparatus comprises a case 10 in which the electrical, optical and physical elements of the colorimeter are conveniently mounted.

Two or more apertures are provided in the top surface 12 of the case 10. One opening 14 is provided with a collar 16 into which a test tube or other glass vial V can be inserted. A stand 18 inside the case 10 is adapted to support glass vial V while a sample in vial V is being read in the stationary mode.

A second aperture 20 is provided at another location in surface 12, adapted to receive a flow through cuvette C having a funnel shaped top and a generally thin planar body comprising two flat faces and a space between them through which the sample flows while it is being read.

A lamp or other light source 30 is disposed inside case 10 in a location which permits it to illuminate either vial V or cuvette C. A support 22 is provided to receive a replaceable filter 24 which permits selection of the wave lengths of the illumination provided by lamp 30 to vial V or cuvette C. A resistor 40 is connected in series with a transformer 42 and lamp 30 so that the intensity of illumination may be adjusted as required. Of course two light sources and two separate optical systems may be used if this is preferred.

A light sensitive receiver 42' is positioned inside case 10 so as to receive the residue of illumination which is not absorbed by the sample in either vial V or cuvette C, said receiver 42' conducting a current which is dependent on the amount of light it receives. The current conducted by the resistor-photoconductive cell 42' causes a pointer 44 on a meter 46 to tranverse the face of the meter 46 and provide a readout of the characteristic of the sample being measured.

By throwing a switch 48 mounted on the meter, and connected to a shutter or other means in the case 10, lamp 30 or other light source is activated to illuminate either vial V or cuvette C and the sample contained therein, and as a result, light is absorbed in the sample. The radiation which is not absorbed passes through to the resistor-photoconductive cells 42' both of which are electrically connected to the same meter 46. A hose H connects cuvette C with a receptacle B for collecting sample after it has run through the cuvette. The bottle B permits a siphon to be maintained and thus control of the flow through the cuvette is achieved.

It will be seen that the present apparatus provides in a simple and compact form means for performing analyses on a variety of materials, particularly meat and meat products, for the purpose of assaying collagen, nitrite or other constituents therein, by methods known in the art and published for example by the Association of Analytical Chemists (AOAC), whereby either a flow through sample may be analyzed or a sample in a vial may be analyzed.

I claim:

1. In an apparatus for analyzing materials in which filtered radiation is caused to fall upon a sample to be analyzed and at least a portion of said illumination is absorbed by said sample and the balance of said radiation passes through said sample and falls upon a resistor-photoconductive cell thereby producing an electrical output which can be measured, the improvement which comprises providing in said apparatus two separate cuvettes one of which is adapted to receive a sample for analysis at rest and the other of which is adapted to receive a sample flowing through said cuvette for analysis, two resistor-photoconductive cells each of which receives radiation passing through one of said two cuvettes, and means positioned between the means providing said filtered radiation and said cuvettes for selectively directing said radiation to one or the other of said cuvettes thereby permitting a sample to be analysed by either mode of analysis.

2. The apparatus of claim 1 wherein the apparatus includes siphon means operatively connected to the cuvette adapted to receive a sample flowing through said cuvette to thereby control the flow of material through the cuvette during analysis of said material.

* * * * *